United States Patent [19]

Flanigen et al.

[11] Patent Number: 4,952,383

[45] Date of Patent: Aug. 28, 1990

[54] BORON-ALUMINUM-PHOSPHORUS-OXIDE MOLECULAR SIEVE COMPOSITIONS

[75] Inventors: Edith M. Flanigen, White Plains; Brent M. T. Lok, New City; Robert L. Patton, Katonah; Stephen T. Wilson, Shrub Oak, all of N.Y.; Richard T. Gajek., New Fairfield, Conn.

[73] Assignee: UOP, Des Plaines, Ill.

[21] Appl. No.: 29,540

[22] Filed: Mar. 24, 1987

Related U.S. Application Data

[63] Continuation-in-part of Ser. No. 804,248, Dec. 4, 1985, abandoned, which is a continuation of Ser. No. 599,812, Apr. 13, 1984, abandoned.

[51] Int. Cl.$^5$ ............................................. C01B 35/10
[52] U.S. Cl. ............................................. 423/277
[58] Field of Search ............... 423/306, 328, 329, 305, 423/279, 277; 502/208, 202

[56] References Cited

U.S. PATENT DOCUMENTS

| 4,310,440 | 1/1982 | Wilson et al. | 423/305 |
| 4,420,467 | 12/1983 | Whittam | 423/328 |
| 4,440,871 | 4/1984 | Lok et al. | 502/214 |
| 4,456,582 | 6/1984 | Marosi et al. | 423/277 |

FOREIGN PATENT DOCUMENTS

| 1182099 | 2/1985 | Canada . | |
| 0042226 | 12/1981 | European Pat. Off. | 423/326 |
| 0054364 | 6/1982 | European Pat. Off. . | |
| 0055046 | 6/1982 | European Pat. Off. . | |
| 0055529 | 7/1982 | European Pat. Off. . | |
| 0059059 | 9/1982 | European Pat. Off. . | |
| 3134317 | 3/1983 | Fed. Rep. of Germany | 423/328 |

OTHER PUBLICATIONS

Haggin, "Aluminophosphates Broaden Shape Selective Catalyst Types", C&EN, Jun. 20, 1983, pp. 36-37.

*Primary Examiner*—Robert L. Stoll
*Assistant Examiner*—R. Bruce Breneman
*Attorney, Agent, or Firm*—Thomas K. McBride; Eugene I. Snyder; Frank S. Molinaro

[57] ABSTRACT

Molecular sieves having three-dimensional microporous framework structures of $BO_2$, $AlO_2$ and $PO_2$ tetrahedral units are disclosed. These molecular sieves have an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$; and "x", "y" and "z" represent the mole fractions of boron, aluminum and phosphorus, respectively, present as tetrahedral oxides. The use of these molecular sieves as adsorbents, catalysts etc. is also disclosed.

65 Claims, 3 Drawing Sheets

BORON-ALUMINUM-PHOSPHORUS-OXIDE MOLECULAR SIEVE COMPOSITIONS

CROSS-REFERENCE TO RELATED APPLICATIONS

This application is a continuation-in-part of our co-pending application Ser. No. 802,248, filed Dec. 4, 1985 now abandoned which in turn is a continuation of application Ser. No. 599,812 filed Apr. 13, 1984 and now abandoned.

FIELD OF THE INVENTION

The instant invention relates to a novel class of crystalline microporous molecular sieves and to the method of their preparation. The invention relates to novel boron-aluminum-phosphorus-oxide molecular sieves containing framework tetrahedral oxide units of boron, aluminum and phosphorus. These compositions may be prepared hydrothermally from gels containing reactive compounds of boron, aluminum and phosphorus capable of forming framework tetrahedral oxides, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In U.S. Pat. No. 4,440,871 there is described a novel class of silicon-substituted aluminophosphates which are both microporous and crystalline. The materials have a three-dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR: (Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In U.S. Pat. No. 4,500,651, there is described a novel class of titanium-containing molecular sieves whose chemical composition in the as-synthesized and anhydrous form is represented by the unit empirical formula:

$$mR: (Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In U.S. Pat. No. 4,567,029, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; and "M" represents at least one metal of the group magnesium, manganese, zinc and cobalt; "x", "y", and "z" represent the mole fractions of the metal "M", aluminum and phosphorus, respectively, present as tetrahedral oxides.

In U.S. Pat. No. 4,544,143, there is described a novel class of crystalline ferroaluminophosphates having a three-dimensional microporous framework structure of $FeO_2$, $AlO_2$ and $PO_2$ tetrahedral units and having an empirical chemical composition on an anhydrous basis expressed by the formula:

$$mR: (Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fractions of the iron, aluminum and phosphorus, respectively, present as tetrahedral oxides.

The instant invention relates to new molecular sieve compositions having framework tetrahedral units of $BO_2^-$, $AlO_2^-$ and $PO_2^-$.

SUMMARY OF THE INVENTION

Figure 1:
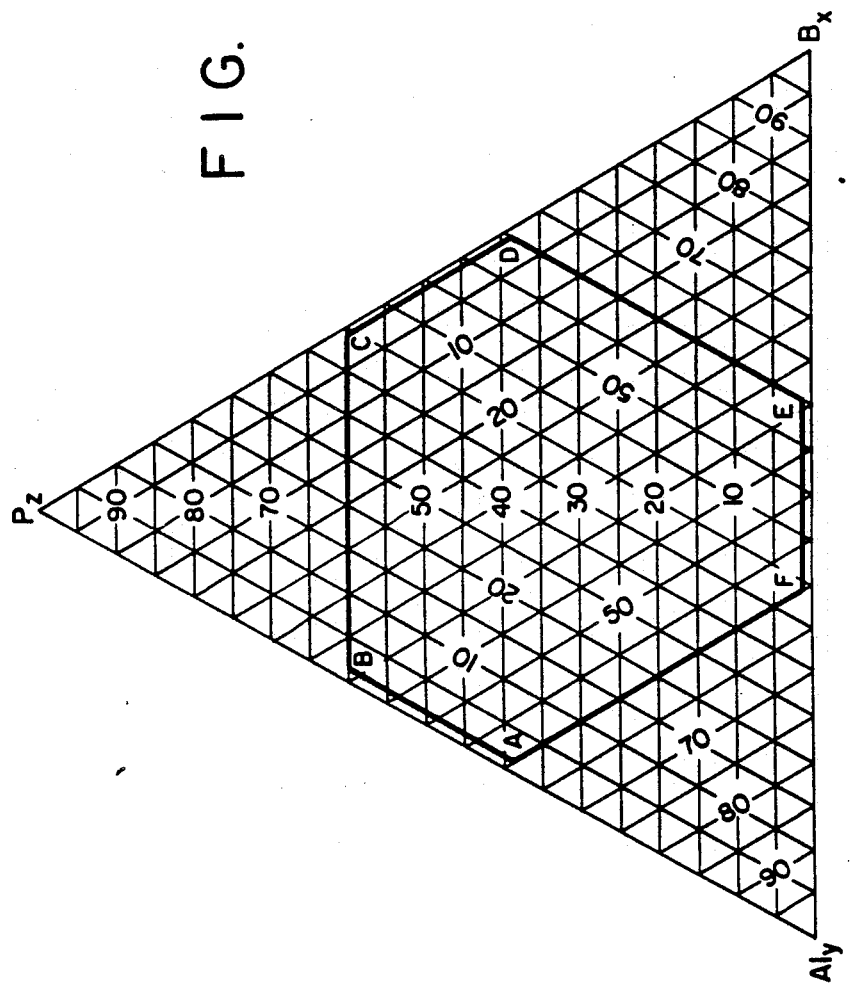
FIG. 1 is a ternary diagram wherein parameters relating to the instant compositions are set forth as mole fractions.

The instant invention relates to a new class of boron-aluminum-phosphorus-oxide molecular sieves having a crystal framework structure of $BO_2^-$, $AlO_2^-$ and $PO_2^+$ tetrahedral oxide units. These new molecular sieves exhibit ion-exchange, adsorption and catalytic properties and, accordingly, find wide use as adsorbents and catalysts. The members of this novel class of compositions have crystal framework structures of $BO_2^-$, $AlO_2^-$ and $PO_2^+$ tetrahedral units and have an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; and "x", "y" and "z" represent the mole fractions of boron, aluminum and phosphorus, respectively, present as tetrahedral oxides. These molecular sieve compositions comprise crystalline molecular sieves having a three-dimensional microporous framework structure of $BO_2^-$, $AlO_2^-$ and $PO_2^+$ tetrahedral units.

The molecular sieves of the instant invention will be generally referred to by the acronym "BAPO" to designate the framework of $BO_2^-$, $AlO_2^-$ and $PO_2^+$ tetrahedral units. Actual class members will be identified by denominating the various structural species which make up the BAPO class by assigning a number and, accordingly, are identified as "BAPO-i" wherein "i" is an integer. The given species designation is not intended to denote a similarity in structure to any other species denominated by a numbering system.

DETAILED DESCRIPTION OF THE INVENTION

The instant invention relates to a new class of boron-aluminum-phosphorus-oxide molecular sieves comprising a crystal framework structure of $BO_2^-$, $AlO_2^-$ and $PO_2^+$ tetrahedral oxide units. These new molecular sieves exhibit ion-exchange, adsorption and catalytic properties and, accordingly, find wide use as adsorbents and catalysts. The BAPO molecular sieves have three-dimensional microporous framework structures of $BO_2^-$, $AlO_2^-$ and $PO_2^+$ tetrahedral oxide units having an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; and "x", "y" and "z" represent the mole fractions of boron, aluminum and phosphorus, respectively, present as tetrahedral oxides. The mole fractions "x", "y", and "z" are generally defined as being within the hexagonal compositional area defined by points A, B, C, D, E and F of the ternary diagram of FIG. 1. Points A, B, C, D, E and F of FIG. 1 have the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.39 | 0.01 | 0.60 |
| D | 0.60 | 0.01 | 0.39 |
| E | 0.60 | 0.39 | 0.01 |
| F | 0.39 | 0.60 | 0.01 |

Figure 2:
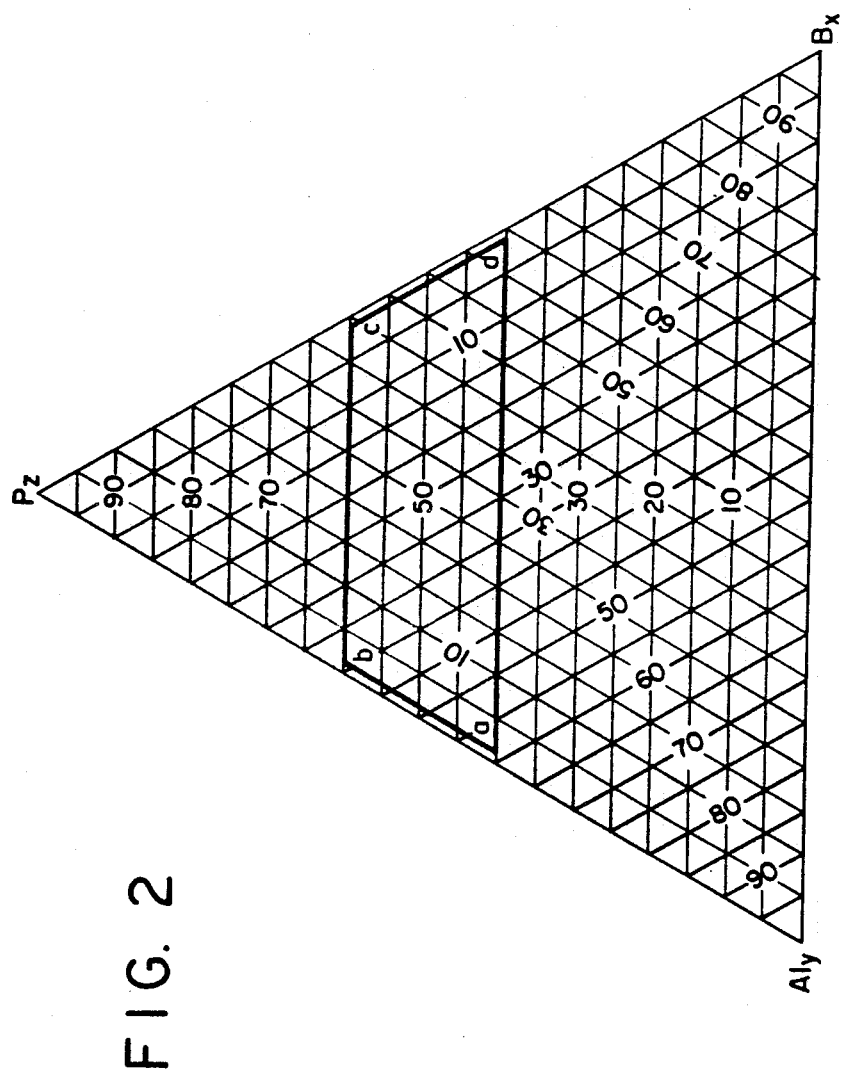
FIG. 2 is a ternary diagram wherein parameters relating to preferred compositions are set forth as mole fractions.

In a preferred subclass of the BAPO molecular sieves, the values of "x", "y" and "z" in the above formula are within the tetragonal compositional area defined by the points a, b, c and d of the ternary diagram which is FIG. 2 of the drawings, said points a, b, c and d representing the following values for "x", "y" and "z":

| Point | Mole Fraction | | |
|---|---|---|---|
| | x | y | z |
| a | 0.01 | 0.59 | 0.40 |
| b | 0.01 | 0.39 | 0.60 |
| c | 0.39 | 0.01 | 0.60 |
| d | 0.59 | 0.01 | 0.40 |

An especially preferred subclass of the BAPO molecular sieves of the invention are those in which the mole fraction, "x", of boron is not greater than about 0.3.

The BAPOs of this invention are useful as adsorbents, catalysts, ion-exchangers, and the like in much the same fashion as aluminosilicates have been employed heretofore, although their chemical and physical properties are not necessarily similar to those observed for aluminosilicates.

BAPO compositions are generally synthesized by hydrothermal crystallization from a reaction mixture containing reactive sources of boron, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure, at a temperature between 50° and 250° C., and preferably between 100° C. and 200° C. until crystals of the BAPO product are obtained, usually a period of from several hours to several weeks. Typical crystallization times are from about 2 hours to about 30 days, with from about 4 hours to about 20 days, and preferably about 1 to about 7 days, being generally employed to obtain crystals of the BAPO products. The product is recovered by any convenient method such as centrifugation or filtration.

Figure 3:
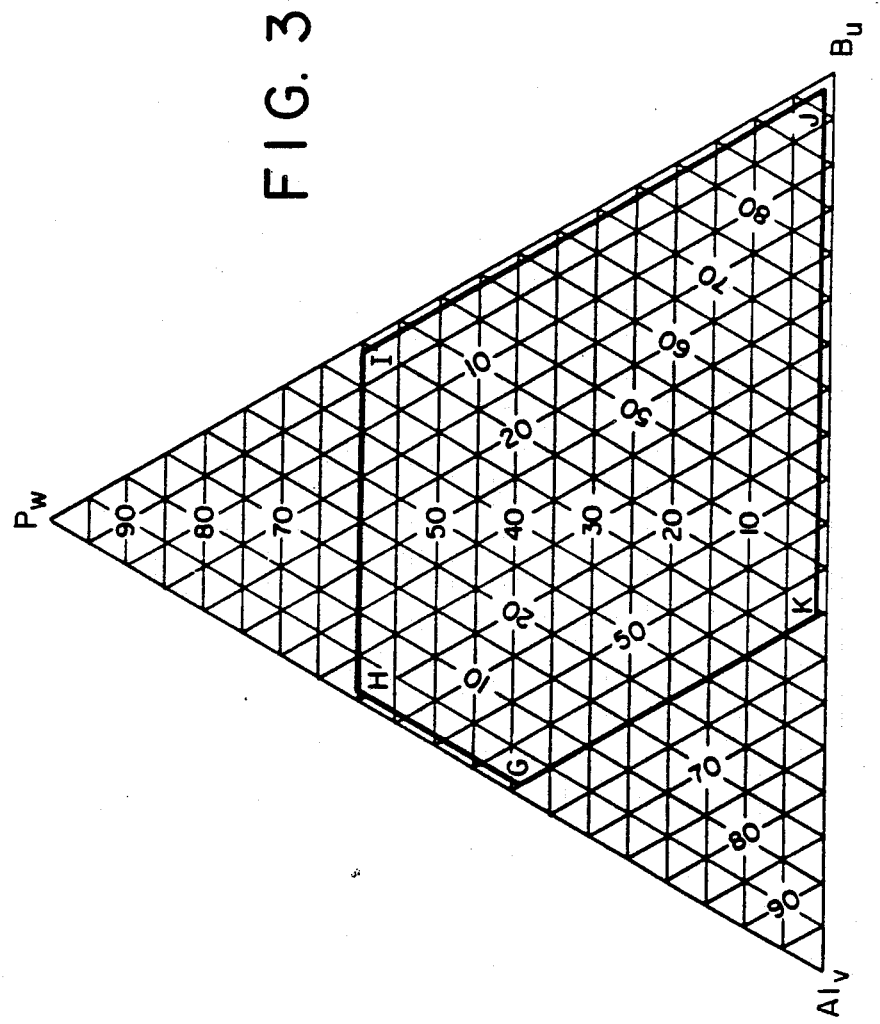
FIG. 3 is a ternary diagram wherein parameters relating to the reaction mixtures employed in the preparation of the compositions of this invention are set forth as mole fractions.

In synthesizing the BAPO compositions of the instant invention, it is preferred to employ a reaction mixture composition expressed in terms of molar oxide ratios as follows:

$$aR: (B_uAl_vP_w)O_2: bH_2O$$

wherein "R" is an organic templating agent; "a" is the amount of organic templating agent "R" and is an effective amount preferably within the range of greater than zero (0) to about 6 and most preferably not more than about 1.0; "b" has a value of from zero (0) to about 500, preferably between about 2 and about 300, desirably not greater than about 20, and most desirably not greater than about 10; and "u", "v" and "w" represent the mole fractions of boron, aluminum and phosphorus, respectively, and each has a value of at least 0.01. The mole fractions "u", "v" and "w" in the reaction mixture are preferably within the pentagonal compositional area defined by points G, H, I, J and K which is shown in FIG. 3 of the drawings, where points G, H, I, J and K have the following values for "u", "v" and "w":

| Point | Mole Fraction | | |
|---|---|---|---|
| | x | y | z |
| G | 0.01 | 0.60 | 0.39 |
| H | 0.01 | 0.39 | 0.60 |
| I | 0.39 | 0.01 | 0.60 |
| J | 0.98 | 0.01 | 0.01 |
| K | 0.39 | 0.60 | 0.01 |

Especially preferred reaction mixtures are those containing from 0.5 to 2.0 moles of $B_2O_3$ and from 0.75 to 1.25 moles of $Al_2O_3$ for each mole of $P_2O_5$.

In the foregoing expression of the reaction composition, the reactants are normalized with respect to the total of $x+y+z=1.00$ mole, whereas in the examples the reaction mixtures are expressed in terms of the molar oxide ratios and may be normalized to 1.00 mole of $P_2O_5$ and/or $Al_2O_3$. This latter form is readily converted to the former form by routine calculation by dividing the total number of moles of boron, aluminum and phosphorus into the moles of each of boron, aluminum and phosphorus. The moles of template and water are similarly normalized by dividing by the total moles of boron, aluminum and phosphorus.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium and quaternary ammonium compounds, the latter two being represented generally by the formula $R_4X^+$, wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired BAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of BAPO, i.e., a single templating agent can, with proper manipulation of the reaction conditions, direct the formation of several BAPO compositions, and a given BAPO composition can be produced using several different templating agents.

The reactive phosphorus source is preferably phosphoric acid, but organic phosphates such as triethyl phosphate may be satisfactory, and so also may crystalline or amorphous aluminophosphates such as the $AlPO_4$ composition of U.S. Pat. No. 4,310,440. Organophosphorus compounds, such as tetrabutylphosphonium bromide, do not apparently serve as reactive sources of phosphorus, but these compounds may function as templating agents. Conventional phosphorus salts, such as sodium metaphosphate, may be used, at least in part, as the phosphorus source, but are not preferred.

The preferred aluminum source is either an aluminum alkoxide, such as aluminum isopropoxide, or pseudo-boehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of boron, can be introduced into the reaction system in any form which permits the formation in situ of a reactive form of boron, i.e., reactive to form the framework tetrahedral oxide unit of boron. Compounds of boron which may be employed include various boric acids, oxides, alkoxides and hydroxides of boron and also chlorides, bromides, iodides, nitrates, sulfates, carboxylates (e.g., acetates and formates) and the like. Particularly preferred boron sources are boric acid and trimethylborate.

As illustrated in some of the Examples below, in some cases it may be advantageous, when synthesizing the BAPO compositions of the present invention, to first combine sources of boron, aluminum and phosphorus to form an amorphous material containing all three elements, and thereafter to heat the amorphous material to produce a crystalline molecular sieve of this invention. It is not necessary that the total quantities of the reactive sources of boron, aluminum and phosphorus to be used in the final reaction mixture be present in the amorphous material, since additional quantities of the elements can be added during the later heat treatment; in particular, it has been found convenient to add additional quantities of phosphorus to the amorphous material before the heat treatment. The preliminary formation of the amorphous material assists in the incorporation of the boron into the final molecular sieve.

While not essential to the synthesis of BAPO compositions, stirring or other moderate agitation of the reaction mixture and/or seeding the reaction mixture with seed crystals of either the BAPO species to be produced or a topologically similar aluminophosphate, aluminosilicate or molecular sieve composition, facilitates the crystallization procedure.

After crystallization the BAPO product may be isolated and advantageously washed with water and dried in air. Caution should be exercised, however, in selecting the washing technique employed since it has been found that in the BAPO aluminophosphates, as in borosilicates, the boron in the framework tends to be somewhat labile and may be partially removed by certain washing procedures. Guidance as to appropriate washing procedures to avoid removal of boron from the framework of the BAPO molecular sieves may be obtained from the Examples below. The as-synthesized BAPO generally contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular BAPO species. As a general rule the templating agent, and hence the occluded organic species, is too large to move freely through the pore system of the BAPO product and must be removed by calcining the BAPO at temperatures of 200° to 700° C., preferably about 350° to about 600° C., to thermally degrade the organic species. In a few instances the pores of the BAPO product are sufficiently large to permit transport of the templating agent, particularly if the latter is a small molecule, and accordingly complete or partial removal thereof can be accomplished by conventional desorption procedures such as those carried out in the case of zeolites. It will be understood that the term "as-synthesized" as used herein does not include the condition of the BAPO phase wherein the organic moiety occupying the intracrystalline pore system as a result of the hydrothermal crystallization process has been reduced by post-synthesis treatment such that the value of "m" in the composition formula

mR: $(B_xAl_yP_z)O_2$ has a value of less than 0.02. The other symbols of the formula are as defined hereinabove. In those preparations in which an alkoxide is employed as the source of boron, aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized BAPO material.

Since the present BAPO compositions are formed from $BO_2$, $AlO_2$ and $PO_2$ tetrahedral units which, respectively, have a net charge of $-1$, $-1$ and $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of boron present in the reaction mixture, or an organic cation derived from the templating agent. Similarly, a $BO_2^-$ tetrahedron can be balanced electrically by association with $PO_2^+$ tetrahedra, a cation of boron present in the reaction mixture, a simple cation such as an alkali metal cation, a proton ($H^+$), organic cations derived from the templating agent, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington DC (1971)].

The BAPO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of BAPO compositions will generally be possible only after any organic moiety derived from the template, present as a result of synthesis, has been removed from the pore system. Dehydration to remove water present in the as-synthesized BAPO compositions can usually be accomplished, to some degree at least, in the usual manner without removal of the organic moiety, but the absence of the organic species greatly facilitates adsorption and desorption procedures. The BAPO materials have various degrees of hydrothermal and thermal stability, some being quite remarkable in this regard, and function as molecular sieve adsorbents and hydrocarbon conversion catalysts or catalyst bases.

In preparing the BAPO composition it is preferred to use a stainless steel reaction vessel lined with an inert plastic material, e.g., polytetrafluoroethylene, to avoid contamination of the reaction mixture. In general, the final reaction mixture from which each BAPO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, it is preferred that the intermediate mixtures as well as the final reaction mixtures be stirred until substantially homogeneous.

X-ray patterns of reaction products are obtained by X-ray analysis using standard X-ray powder diffraction techniques. The radiation source is a high-intensity, copper target, X-ray tube operated at 50 Kv and 40 ma.

The diffraction pattern from the copper K-alpha radiation and graphite monochromator is suitably recorded by an X-ray spectrometer scintillation counter, pulse height analyzer and strip chart recorder. X-ray patterns are obtained using flat compressed powder samples which are scanned at 2° (2 theta) per minute, using a two second time constant. Interplanar spacings (d) in Angstrom units are obtained from the position of the diffraction peaks expressed as 2Θ where Θ is the Bragg angle as observed on the strip chart. Intensities are determined from the heights of diffraction peaks after subtracting background, "$I_o$" being the intensity of the strongest line or peak, and "I" being the intensity of each of the other peaks. Alternatively, the X-ray patterns may be obtained by use of computer based techniques using two Siemens D-500 X-ray powder diffractometers with copper K-alpha radiation and Siemens type K-805 X-ray sources, such being available from Siemens Corporation, Cherry Hill, New Jersey.

As will be understood by those skilled in the art the determination of the parameter 2 theta is subject to both human and mechanical error which, in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their X-ray powder diffraction patterns and as such may have one of the X-ray patterns set forth in the following Tables A through V, wherein said X-ray patterns are for the as-synthesized form unless otherwise noted. In most cases, the pattern of the corresponding calcined form will also fall within the relevant Table. However, in some cases the removal of the occluded templating agent which occurs during calcination will be accompanied by sufficient relaxation of the lattice to shift some of the lines slightly outside the ranges specified in the relevant Table. In a small number of cases, calcination appears likely to cause more substantial distortions in the crystal lattice, and hence more significant changes in the X-ray powder diffraction pattern.

TABLE A

| 2Θ | (BAPO-5) d (Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B1*

| 2Θ | (BAPO-11) d (Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

*as-synthesized form

TABLE B2*

| 2Θ | (BAPO-11) d (Å) | Relative Intensity |
|---|---|---|
| 8.0–8.2 | 11.05–10.78 | w–s |
| 9.5–9.9 | 9.31–8.93 | m–s |
| 16.0–16.2 | 5.54–5.47 | s–vs |
| 21.6–21.9 | 4.12–4.06 | vs |
| 22.1–22.6 | 4.02–3.93 | m–s (doublet) |
| 23.4–23.7 | 3.80–3.75 | m–s |

*calcined form

TABLE C

| 2Θ | (BAPO-14) d (Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| 2Θ | (BAPO-16) d (Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E

| 2Θ | (BAPO-17) d (Å) | Relative Intensity |
|---|---|---|
| 7.7–7.8 | 11.5–11.3 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| 2Θ | (BAPO-18) d (Å) | Relative Intensity |
|---|---|---|
| 9.6–9.65 | 9.21–9.16 | vs |
| 15.5–15.6 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| 2Θ | (BAPO-20) d (Å) | Relative Intensity |
|---|---|---|
| 13.7–14.25 | 6.46–6.22 | m–vs |
| 19.55–20.0 | 4.54–4.44 | w–s |

TABLE G-continued

| 2θ | (BAPO-20) d (Å) | Relative Intensity |
|---|---|---|
| 24.05–24.5 | 3.70–3.63 | m–vs |
| 34.3–35.0 | 2.614–2.564 | vw–w |
| 42.5–43.0 | 2.127–2.103 | vw–w |

TABLE H

| 2θ | (BAPO-31) d (Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

| 2θ | (BAPO-33) d (Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| 2θ | (BAPO-33) d(Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| 2θ | (BAPO-34) d(Å) | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

TABLE M

| 2θ | (BAPO-35) d(Å) | Relative Intensity |
|---|---|---|
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| 2θ | (BAPO-36) d(Å) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |

TABLE N-continued

| 2θ | (BAPO-36) d(Å) | Relative Intensity |
|---|---|---|
| 22.2–22.5 | 4.00–3.95 | w–m |

TABLE O

| 2θ | (BAPO-37) d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| 2θ | (BAPO-39) d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| 2θ | (BAPO-40) d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| 2θ | (BAPO-41) d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| 2θ | (BAPO-42) d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| 2θ | (BAPO-44) d(Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

| | (BAPO-46) | |
|---|---|---|
| 2θ | d(Å) | Relative Intensity |
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| | (BAPO-47) | |
|---|---|---|
| 2θ | d(Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

The exact nature of the BAPO molecular sieves is not entirely understood at present, although all are believed to contain $BO_2$, $AlO_2$ and $PO_2$ tetrahedra in the three-dimensional microporous framework structure. The low level of boron present in some of the instant molecular sieves makes it difficult to ascertain the exact nature of the interactions among boron, aluminum and phosphorus. As a result, although it is believed that $BO_2$ tetrahedra are present in the three-dimensional microporous framework structure, it is appropriate to characterize certain BAPO compositions in terms of the molar ratios of oxides, as has been done in some of the examples below.

The following examples are provided to further illustrate the invention and are not intended to be limiting thereof:

EXAMPLE 1

(Preparation of BAPO-5)

(a) BAPO-5 is prepared from a reaction mixture having a composition, expressed in terms of the molar oxide ratios of the components of the reaction mixture, of:

1.0–2.0 TPA: 0.05–0.2 $B_2O_3$: 0.5–1.0 $Al_2O_3$: 0.5–1.0 $P_2O_5$: 40–100 $H_2O$ where "TPA" denotes tripropylamine.

The reaction mixture is digested by placing the reaction mixture in a sealed stainless steel pressure vessel and heating it at an effective temperature and for an effective time to produce the BAPO-5 product. Solids are then recovered by filtration, washed with water and dried in air at room temperature.

The BAPO-5 product's chemical analysis shows the BAPO-5 product contains boron, aluminum and phosphorus in amounts within the hexagonal compositional area defined by points A, B, C, D, E and F of FIG. 1.

The X-ray powder diffraction pattern of a BAPO-5 product is characterized by the following data:

| 2θ | d(Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

(b) The X-ray powder diffraction pattern for a calcined BAPO-5 is also characterized by the X-ray pattern of part (a).

(c) When the calcined BAPO-5 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter (Å) | Pressure (Torr) | Temp, °C. | Wt. % Adsorbed* |
|---|---|---|---|---|
| $O_2$ | 3.46 | 100 | −183 | 7 |
| $O_2$ | 3.46 | 750 | −183 | 10 |
| Neopentane | 6.0 | 700 | 24 | 4 |
| $H_2O$ | 2.65 | 4.3 | 24 | 4 |
| $H_2O$ | 2.65 | 20.0 | 24 | 12 |

*typical amount adsorbed

The pore diameter of BAPO-5 is greater than 6.2 Å.

EXAMPLE 2

(Preparation of BAPO-5)

This preparation of BAPO-5 is published in Appleyard et al., "$^{27}Al$, $^{31}P$ and $^{11}B$ MAS n.m.r. studies of BAPO-5, the boron-substituted analogue of the aluminophosphate molecular sieve, ALPO$_4$-5", Zeolites, 6, 428 (November, 1986).

A BAPO-5 sample was synthesized hydrothermally from a reactive mixture consisting of an aluminum source (pseudo-boehmite), a solution of orthophosphoric acid, a source of boron (boric acid) and a triethylamine (Et$_3$N). An aluminophosphate gel was first formed, to which was added the source of boron and the organic templating agent. Reaction conditions were similar to those normally used in zeolite synthesis except that acidic rather than alkaline solutions were involved. The template was removed from the crystalline product by calcination (heating in air at 600° C. for several hours). X-ray powder diffraction data for the as-synthesized molecular sieve correspond to those reported in European Patent Application Publication No. 158,976 (1985).

The sample analyzed to give relative proportions as:

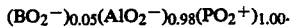

$^{11}B$ MAS n.m.r. spectra of the as-synthesized and calcined forms of the BAPO-5 showed the presence of a single resonance line at δ= −1.1 and −0.5 ppm. for the as-synthesized and calcined forms respectively, indicating that the boron atoms are tetrahedrally coordinated, i.e. present in the framework. This spectrum is not consistent with trigonally coordinated (extra-lattice) boron, in which case, as was observed for boron-ZSM-5 zeolite (see Scholle and Veeman, Zeolites, 5, 110 (1985)) the $^{11}B$ n.m.r. signal is no longer a single narrow resonance but a typical quadrupolar pattern.

EXAMPLES 3 AND 4

These Examples, although producing products containing only small proportions of boron, illustrate techniques which may be used for preparing BAPO molecular sieves of the present invention.

EXAMPLE 3

(Preparation of BAPO-5)

To prepare BAPO-5, a reaction mixture was formed by combining 23.1 grams of 85 wt. percent orthophosphoric acid ($H_3PO_4$) with 41.7 grams of water, adding to the resultant solution 13.8 grams of hydrated aluminum oxide in the form of a pseudo-boehmite phase comprising 74.2 wt. percent of $Al_2O_3$ and 25.8 wt. percent $H_2O$, and stirring the resultant mixture until it was homogeneous. To this homogeneous mixture was added with stirring 6.23 grams of trimethylborate. Finally, there were added to the reaction mixture 22.1 grams of tri-n-propylamine (TPA), and the resultant mixture was stirred until homogeneous. The composition of the final reaction mixture thus produced, expressed in terms of the molar oxide ratios of the components of the reaction mixture, was:

1.5 TPA: 0.6 $B_2O_3$: 1.0 $Al_2O_3$: 1.0 $P_2O_5$: 3.6 MeOH: 30.0 $H_2O$.

A portion of this final reaction mixture was digested by sealing it in a stainless steel pressure vessel lined with polytetrafluoroethylene and heating it in an oven at 150° C. under autogenous pressure for 48 hours. The solid reaction product (which was determined by the analyses described below to be at least partially BAPO-5) was recovered by filtration, washed with water and dried in air at 100° C. for one hour.

A sample of this solid reaction product was analyzed and the following chemical analysis obtained:

| Component | Weight percent |
| --- | --- |
| Carbon | 6.6 |
| $B_2O_3$ | 0.215 |
| $Al_2O_3$ | 34.3 |
| $P_2O_5$ | 50.3 |
| LOI* | 14.8 |

*LOI indicates loss on ignition.

The above chemical analysis corresponds to a product composition in molar oxide ratios of:

0.20 TPA: 0.0092 $B_2O_3$: 1.00 $Al_2O_3$: 1.05 $P_2O_5$: 0.8 $H_2O$ which corresponds to an empirical chemical composition, on an anhydrous basis of:

0.049 TPA: $(B_{0.005}Al_{0.486}P_{0.510})O_2$.

The X-ray powder diffraction pattern of the major component of the product, as synthesized, was characterized by the data in the following Table AA (The Table designated AA contains all the peaks set forth in Table A above, and similarly for Table FA, while, for example, a Table designated B1A contains all the peaks set forth in Table B1 above):

TABLE AA

| (BAPO-5) | | |
| --- | --- | --- |
| $2\theta$ | d(Å) | Relative Intensity $100 \times I/I_o$ |
| 7.49 | 11.80 | 100 |
| 13.0 | 6.83 | 11 |
| 15.0 | 5.91 | 16 |
| 19.9 | 4.46 | 38 |
| 21.1 | 4.21 | 35 |
| 22.5 | 3.95 | 61 |
| 24.8 | 3.59 | 2 |
| 26.1 | 3.42 | 22 |
| 29.1 | 3.06 | 10 |
| 30.2 | 2.96 | 14 |
| 33.8 | 2.65 | 3 |
| 34.7 | 2.58 | 10 |
| 37.1 | 2.42 | 3 |
| 37.8 | 2.38 | 7 |
| 41.8 | 2.16 | 2 |
| 42.4 | 2.13 | 2 |
| 47.9 | 1.898 | 3 |

The X-ray powder diffraction pattern indicated the product to be well crystallized.

EXAMPLE 4

(Preparation of BAPO-5)

To prepare BAPO-5, a solution was formed by dissolving 12.4 grams of boric acid ($H_3BO_3$) in 58.8 grams of a 25 percent solution of tetraethylammonium hydroxide (TEAOH) in methanol (MeOH). To this solution were added 16.3 grams of a hydrated aluminophosphate ($AlPO_4:xH_2O$ containing 75 wt. percent $AlPO_4$ and 25 wt. percent $H_2O$) obtained from ROC/RIC Chemical Co., Belleville, N.J., followed by 4.9 grams of water. The resultant mixture was stirred to form a homogeneous reaction slurry having a composition, expressed in terms of the molar oxide ratios of the components of the slurry, of:

2.0 TEAOH: 2.0 $B_2O_3$: 1.0 $Al_2O_3$: 1.0 $P_2O_5$: 27.6 MeOH: 10.0 $H_2O$.

A portion of this final reaction slurry was digested by sealing it in a stainless steel pressure vessel lined with polytetrafluoroethylene and heating it in an oven at 200° C. under autogenous pressure for 72 hours. The solid reaction product (which was determined by the analyses described below to contain both BAPO-5 and BAPO-18) was recovered by filtration, washed with water and dried at ambient temperature.

A sample of this solid reaction product was analyzed and the following chemical analysis obtained (no analyses were conducted for carbon, nitrogen or loss on ignition):

| Component | Weight percent |
| --- | --- |
| $B_2O_3$ | 0.24 |
| $Al_2O_3$ | 31.7 |
| $P_2O_5$ | 41.9 | which corresponds to an empirical chemical composition for the oxide framework of:

$(B_{0.006}Al_{0.510}P_{0.484})O_2$.

The X-ray powder diffraction pattern of the major component of the product, as synthesized, was characterized by the pattern shown in Table AA above, thus indicating that this major component was BAPO-5; the X-ray powder diffraction pattern also indicated the presence of a minor component of BAPO-18 having the pattern shown in Table FA (see Example 7 below).

EXAMPLE 5

(Preparation of BAPO-11)

This Example illustrates the synthesis of BAPO-11 via the preliminary formation of an amorphous material containing boron, aluminum and phosphorus, and also illustrates the effects of various washing techniques on the boron content of the product.

(a) To prepare BAPO-11, a solution was formed by combining 38.4 grams of 85 wt. percent orthophosphoric acid ($H_3PO_4$) with 38.7 grams of water, and adding to the resultant solution 34.6 grams of trimethylborate. To the resultant mixture were added 23.0 grams of hydrated aluminum oxide in the form of a pseudo-boehmite phase comprising 74.2 wt. percent of $Al_2O_3$ and 25.8 wt. percent H2O, and the resultant mixture was stirred until it was homogeneous. Finally, there were added to the reaction mixture with stirring 34.0 grams of di-n-propylamine (DPA), and the resultant mixture was stirred until homogeneous. The composition of the final reaction mixture thus produced, expressed in terms of the molar oxide ratios of the components of the reaction mixture, was:

2.0 DPA: 1.0 $B_2O_3$: 1.0 $Al_2O_3$: 1.0 $P_2O_5$: 6.0 MeOH: 20.0 $H_2O$.

A portion of this final reaction mixture was digested by sealing it in a stainless steel pressure vessel lined with polytetrafluoroethylene and heating it in an oven at 200° C. under autogenous pressure for 24 hours to obtain an unwashed product slurry.

(b) One portion of the product slurry from part (a) above was washed with water, filtered and dried in air at ambient temperature.

A sample of this solid reaction product was analyzed and the following chemical analysis obtained:

| Component | Weight percent |
|---|---|
| Carbon | 4.9 |
| Nitrogen | 0.93 |
| $B_2O_3$ | 0.14 |
| $Al_2O_3$ | 36.0 |
| $P_2O_5$ | 56.1 |
| LOI* | 8.0 |

*LOI indicates loss on ignition.

The above chemical analysis corresponds to a product composition in molar oxide ratios of:

0.19 DPA: 0.006 $B_2O_3$: 1.00 $Al_2O_3$: 1.12 $P_2O_5$: 0.19 $H_2O$ which corresponds to an empirical chemical composition, on an anhydrous basis of:

0.045 DPA: $(B_{0.003}Al_{0.470}P_{0.527})O_2$.

The X-ray powder diffraction pattern of the major component of the product, as synthesized, was characterized by the data in the following Table B1A:

TABLE B1A (BAPO-11)

| $2\theta$ | d(Å) | Relative Intensity 100 × $I/I_o$ |
|---|---|---|
| 8.1 | 10.877 | 47 |
| 9.5 | 9.33 | 78 |
| 13.3 | 6.67 | 22 |
| 15.7 | 5.63 | 47 |
| 16.3 | 5.42 | 7 |
| 19.1 | 4.66 | 8 |
| 20.5 | 4.33 | 60 |
| 21.1 | 4.21 | 100 |
| 21.9 | 4.07 | 7 |
| 22.2 | 4.00 | 63 |
| 22.6 | 3.93 | 59 |
| 22.8 | 3.90 | 62 |
| 23.3 | 3.82 | 90 |
| 24.6 | 3.62 | 7 |
| 24.8 | 3.59 | 10 |
| 26.4 | 3.37 | 13 |
| 26.7 | 3.34 | 21 |
| 28.4 | 3.14 | 6 |
| 28.7 | 3.11 | 17 |
| 29.2 | 3.06 | 5 |
| 29.6 | 3.02 | 8 |
| 31.6 | 2.83 | 10 |
| 33.0 | 2.71 | 18 |
| 34.3 | 2.61 | 12 |
| 35.9 | 2.50 | 3 |
| 36.6 | 2.45 | 7 |
| 37.7 | 2.39 | 9 |
| 37.9 | 2.37 | 12 |
| 39.5 | 2.28 | 4 |

(c) Another portion of the product slurry from part (a) above was (without washing) dried in an oven at 200° C. The X-ray powder diffraction pattern of the product was characterized by the data in the following Table B2B:

TABLE B2B (BAPO-11)

| $2\theta$ | d(Å) | Relative Intensity 100 × $I/I_o$ |
|---|---|---|
| 8.1 | 10.92 | 73 |
| 9.6 | 9.22 | 60 |
| 9.8 | 9.02 | 66 |
| 12.8 | 6.90 | 33 |
| 13.1 | 6.76 | 16 |
| 16.1 | 5.51 | 73 |
| 19.5 | 4.55 | 12 |
| 19.9 | 4.46 | 30 |
| 20.3 | 4.38 | 14 |
| 21.3 | 4.17 | 32 |
| 21.8 | 4.07 | 100 |
| 22.2 | 4.00 | 63 |
| 22.4 | 3.96 | 72 |
| 23.0 | 3.86 | 23 |
| 23.5 | 3.79 | 65 |
| 24.0 | 3.71 | 14 |
| 25.8 | 3.45 | 21 |
| 27.7 | 3.22 | 15 |
| 27.9 | 3.20 | 12 |
| 29.6 | 3.01 | 22 |
| 29.8 | 3.00 | 26 |
| 30.4 | 2.94 | 14 |
| 31.8 | 2.81 | 10 |
| 32.7 | 2.74 | 29 |

(d) The dried product from part (c) above was calcined in air for 2 hours at 500° C. and allowed to rehydrate under ambient conditions.

A sample of this solid reaction product was analyzed and the following chemical analysis obtained:

| Component | Weight percent |
|---|---|
| Carbon | 1.6 |
| B₂O₃ | 14.2 |
| Al₂O₃ | 25.5 |
| P₂O₅ | 41.9 |
| H₂O | 18.5 |

(The low carbon content indicates that nearly all of the initial di-n-propylamine was decomposed and removed by the calcination.)

(The low carbon content indicates that nearly all of the initial di-n-propylamine was decomposed and removed by the calcination.)

The above chemical analysis corresponds to a product composition in molar oxide ratios of:

0.82 $B_2O_3$:1.00 $Al_2O_3$:1.18 $P_2O_5$ which corresponds to an empirical chemical composition, on an anhydrous basis of:

$(B_{0.27}Al_{0.33}P_{0.40})O_2$.

The X-ray powder diffraction pattern of the major component of the calcined product was characterized by the data in the following Table B2C:

TABLE B2C (BAPO-11)

| 2θ | d(Å) | Relative Intensity 100 × I/I₀ |
|---|---|---|
| 8.1 | 10.94 | 21 |
| 9.9 | 8.98 | 51 |
| 12.8 | 6.89 | 27 |
| 14.7 | 6.03 | 19 |
| 16.1 | 5.49 | 77 |
| 19.5 | 4.54 | 12 |
| 19.9 | 4.46 | 32 |
| 21.9 | 4.06 | 100 |
| 22.2 | 4.00 | 48 |
| 22.5 | 3.95 | 57 |
| 23.6 | 3.77 | 61 |
| 24.0 | 3.70 | 13 |
| 24.3 | 3.66 | 13 |
| 25.8 | 3.45 | 24 |
| 26.8 | 3.33 | 11 |
| 27.3 | 3.27 | 13 |
| 28.1 | 3.18 | 50 |
| 29.8 | 3.00 | 27 |
| 30.4 | 2.94 | 16 |
| 32.7 | 2.74 | 27 |

(e) A 1.2 gram portion of the calcined product from part (d) above was washed by first stirring it for 16 hours in 50 grams of isopropanol, then filtering, washing with 200 grams of water, re-filtering, and finally drying at 100° C.

A sample of the resultant product was analyzed and the following chemical analysis obtained:

| Component | Weight percent |
|---|---|
| B₂O₃ | 2.46 |
| Al₂O₃ | 30.5 |
| P₂O₅ | 47.8 |
| LOI* | 19.6 |

*LOI indicates loss on ignition.

The above chemical analysis corresponds to a product composition in molar oxide ratios, excluding carbonaceous residues and water, of:

0.12 $B_2O_3$:1.00 $Al_2O_3$:1.13 $P_2O_5$ which corresponds to an empirical chemical composition, on an anhydrous basis, of:

$(B_{0.05}Al_{0.45}P_{0.50})O_2$.

(f) A sample of the product produced in part (b) was calcined in air at 500° C. for one hour. This calcined sample, and samples of the products produced in parts (d) and (e) above were utilized in adsorption capacity studies using a standard McBain-Bakr gravimetric adsorption apparatus. Before being used in the adsorption tests, the samples were activated by heating to 350° C. overnight. The following data were generated in the adsorption studies:

| Adsorbate | Kinetic Diameter (Å) | Pressure (Torr) | Temp. °C. | Wt. % Adsorbed (b) | (d) | (e) |
|---|---|---|---|---|---|---|
| O₂ | 3.46 | 100 | −183 | 10.1 | 1.1 | 5.7 |
| Cyclohexane | 6.0 | 60 | 22 | 7.0 | n | 4.4 |
| Neopentane | 6.2 | 101 | 22 | 0.4 | n | 0.6 |
| Neopentane | 6.2 | 750 | 22 | 2.2 | n | 1.9 |
| H₂O | 2.65 | 4.6 | 22 | 12.8 | n | 12.7 | n-denotes not tested

From the above data, the products produced in parts (b) and (e) above were determined to be microporous molecular sieves with a pore size greater than about 6.0 Å, as shown by the adsorption of cyclohexane (kinetic diameter of 6.0 Å) but less than or near 6.2 Å, as shown by the pressure dependent adsorption of neopentane (kinetic diameter of 6.2 Å).

(g) Another portion of the product slurry prepared in part (a) above was digested by sealing it in a stainless steel pressure vessel lined with polytetrafluoroethylene and heating it in an oven at 200° C. under autogenous pressure for 72 hours. The solid reaction product was recovered by filtration, washed with water and dried.

The X-ray powder diffraction pattern of the major component of the product, as synthesized, was essentially that set forth in Table B1A above; the pattern indicated that the product was well-crystallized.

EXAMPLE 6

(Preparation of BAPO-17)

(a) BAPO-17 is prepared from a reaction mixture having a composition, expressed in terms of the molar oxide ratios of the components of the reaction mixture, of:

1.0–2.0 QN:0.05–0.2 $B_2O_3$:0.5–1.0 $Al_2O_3$: 0.5–1.0 $P_2O_5$:40–100 $H_2O$ where "QN" denotes quinuclidine.

The reaction mixture is digested by placing the reaction mixture in a sealed stainless steel pressure vessel and heating it at an effective temperature and for an effective time to produce the BAPO-17 product. Solids are then recovered by filtration, washed with water and dried in air at room temperature.

The BAPO-17 product's chemical analysis shows the BAPO-17 product contains boron, aluminum and phosphorus in amounts within the hexagonal compositional area defined by points A, B, C, D, E and F of FIG. 1.

The X-ray powder diffraction pattern of a BAPO-17 product is characterized by the following data:

| 2θ | d(Å) | Relative Intensity |
|---|---|---|
| 7.7–7.8 | 11.5–11.3 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

(b) The X-ray powder diffraction pattern for a calcined BAPO-17 is also characterized by the X-ray pattern of part(a).

(c) When the calcined BAPO-17 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter(Å) | Pressure (Torr) | Temp, °C. | Wt. % Adsorbed* |
|---|---|---|---|---|
| $O_2$ | 3.46 | 100 | −183 | 10 |
| $O_2$ | 3.46 | 750 | −183 | 12 |
| n-Butane | 4.3 | 100 | 24 | 4 |
| $H_2O$ | 2.65 | 4.3 | 24 | 13 |
| $H_2O$ | 2.65 | 20 | 24 | 14 |

*typical amount adsorbed

The pore diameter of BAPO-17 is about 4.3 Å.

EXAMPLE 7

(Preparation of BAPO-18)

This Example illustrates the synthesis of BAPO-18 via the preliminary formation of an amorphous material containing boron, aluminum and phosphorus.

(a) To prepare BAPO-18, a solution was formed by combining 23.1 grams of 85 wt. percent orthophosphoric acid ($H_3PO_4$) with 9.2 grams of water. Separately, 41.6 grams of aluminum isopropoxide and 20.8 grams of trimethylborate were dispersed in 60.0 grams of isopropanol, and the phosphoric acid solution was added to the resultant mixture with stirring. The composition of the final homogeneous slurry (reaction mixture) thus produced, expressed in terms of the molar oxide ratios of the components of the reaction mixture, was:

1.0 $B_2O_3$:1.0 $Al_2O_3$:1.0 $P_2O_5$:
6.0 MeOH:16 $C_3H_7OH$:10 $H_2O$.

This final homogeneous slurry was allowed to dry overnight at room temperature to yield a dry solid. A sample of this dry solid was analyzed and the following chemical analysis obtained:

| Component | Weight percent |
|---|---|
| $B_2O_3$ | 12.6 |
| $Al_2O_3$ | 26.5 |
| $P_2O_5$ | 30.9 |
| $H_2O$ (by difference) | 30.0 |

The above chemical analysis corresponds to a product composition in molar oxide ratios of:

0.70 $B_2O_3$:1.00 $Al_2O_3$:0.84 $P_2O_5$:6.4 $H_2O$.

Small portions of the solid, with and without calcination at 600° C. for 25 minutes, were subjected to X-ray powder diffraction analysis. No peaks corresponding to presence of any crystalline material were found in either portion.

(b) A 19.3 gram portion of the dry solid produced in from part (a) above was mixed with a solution of 1.7 grams of 85 wt. percent orthophosphoric acid ($H_3PO_4$) in 0.6 grams of water, then 18.4 grams of 40 wt. percent aqueous tetraethylammonium hydroxide (TEAOH) were added and the resultant mixture stirred for five minutes, to form a thick slurry. The composition of the final homogeneous slurry thus produced, expressed in terms of the molar oxide ratios of the components of the slurry, was:

1.0 TEAOH: 0.7 $B_2O_3$:1.0 $Al_2O_3$:1.0 $P_2O_5$:20 $H_2O$.

(c) A portion of the slurry from part (b) above was digested by sealing it in a stainless steel pressure vessel lined with polytetrafluoroethylene and heating it in an oven at 150° C. under autogenous pressure for 96 hours. The solid reaction product (which was determined by the analyses described below to be principally BAPO-18) was recovered by centrifugation, washed with water and dried in air at room temperature.

A sample of this solid reaction product was analyzed and the following chemical analysis obtained:

| Component | Weight percent |
|---|---|
| Carbon | 10.0 |
| $B_2O_3$ | 0.86 |
| $Al_2O_3$ | 31.2 |
| $P_2O_5$ | 46.6 |
| LOI* | 21.5 |

*LOI indicates loss on ignition.

The above chemical analysis corresponds to a product composition in molar oxide ratios of:

0.34 TEAOH:0.040 $B_2O_3$:1.00 $Al_2O_3$:
1.07 $P_2O_5$:1.2 $H_2O$ which corresponds to an empirical chemical composition, on an anhydrous basis of:

0.081 TEAOH: $(B_{0.019}Al_{0.474}P_{0.507})O_2$.

The X-ray powder diffraction pattern of the major component of the product, as synthesized, was characterized by the data in the following Table FA:

TABLE FA

| (BAPO-18) | | |
|---|---|---|
| 2θ | d(Å) | Relative Intensity 100 × I/I_o |
| 9.6 | 9.20 | 100 |
| 10.5 | 8.41 | 4 |
| 11.0 | 8.02 | 4 |
| 13.2 | 6.71 | 6 |
| 14.0 | 6.31 | 5 |
| 14.9 | 5.96 | 4 |
| 15.6 | 5.69 | 24 |
| 17.1 | 5.20 | 44 |
| 17.5 | 5.07 | 6 |
| 17.9 | 4.95 | 7 |
| 19.7 | 4.51 | 4 |
| 20.2 | 4.39 | 18 |
| 21.0 | 4.22 | 38 |
| 22.2 | 4.01 | 10 |
| 24.5 | 3.64 | 8 |
| 24.9 | 3.57 | 5 |

TABLE FA-continued
(BAPO-18)

| 2θ | d(Å) | Relative Intensity 100 × I/I₀ |
|---|---|---|
| 26.2 | 3.40 | 8 |
| 26.5 | 3.36 | 8 |
| 27.0 | 3.31 | 7 |
| 28.2 | 3.17 | 4 |
| 30.1 | 2.97 | 10 |
| 30.8 | 2.90 | 9 |
| 31.4 | 2.85 | 9 |
| 31.8 | 2.81 | 5 |
| 32.5 | 2.76 | 13 |

The X-ray analysis also indicated that the product was well-crystallized.

(d) Another portion of the slurry produced in part (b) above was digested in the same way as in part (c) above, except that the digestion was conducted at 200° C. for 96 hours. The product was isolated in the same way as in part (c) above. X-ray powder diffraction analysis resulted in a slightly less intense pattern which was otherwise essentially identical to that set forth in Table FA above.

(e) A 20 gram portion of the slurry produced in part (b) above was mixed with 18 grams of water to produce a reaction mixture having a composition, expressed in terms of the molar oxide ratios of the components of the reaction mixture, of:

1.0 TEAOH:0.7 $B_2O_3$:1.0 $Al_2O_3$:1.0 $P_2O_5$:60 $H_2O$.

Two separate portions of this reaction mixture were digested, separated, washed and dried in the same way as in part (c) above, except that the digestions were carried at 150° C. for 96 hours, and 200° C. for 24 hours, respectively. X-ray powder diffraction analysis of the products showed them to be impure but containing BAPO-18 having an X-ray diffraction pattern essentially identical to that set forth in Table FA above.

EXAMPLE 8

(Preparation of BAPO-31)

(a) BAPO-31 is prepared from a reaction mixture having a composition, expressed in terms of the molar oxide ratios of the components of the reaction mixture, of:

1.0–2.0 DPA:0.05–0.2 $B_2O_3$:0.5–1.0 $Al_2O_3$: 0.5–1.0 $P_2O_5$:40–100 $H_2O$ where "DPA" denotes di-n-propylamine.

The reaction mixture is digested by placing the reaction mixture in a sealed stainless steel pressure vessel and heating it at an effective temperature and for an effective time to produce the BAPO-31 product. Solids are then recovered by filtration, washed with water and dried in air at room temperature.

The BAPO-31 product's chemical analysis shows the BAPO-31 product contains boron, aluminum and phosphorus in amounts within the hexagonal compositional area defined by points A, B, C, D, E and F of FIG. 1.

The X-ray powder diffraction pattern of a BAPO-31 product is characterized by the following data:

| 2θ | d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

(b) The X-ray powder diffraction pattern for a calcined BAPO-31 is also characterized by the X-ray pattern of part (a).

(c) When the calcined BAPO-31 of part (b) is utilized in adsorption capacity studies using a standard McBain-Bakr gravimetric adsorption apparatus the measurements are made on a sample after activation at 350° C. in vacuum. The following data are used in the adsorption studies:

| Adsorbate | Kinetic Diameter(Å) | Pressure (Torr) | Tmp, °C. | Wt. % Adsorbed* |
|---|---|---|---|---|
| $O_2$ | 3.46 | 100 | −183 | 4 |
| $O_2$ | 3.46 | 750 | −183 | 6 |
| Cyclohexane | 6.0 | 90 | 24 | 3 |
| Neopentane | 6.2 | 700 | 24 | 3 |
| $H_2O$ | 2.65 | 4.3 | 24 | 3 |
| $H_2O$ | 2.65 | 20 | 24 | 10 |

*typical amount adsorbed

The pore diameter of BAPO-31 is greater than about 6.2 Å.

EXAMPLE 9

(Preparation of BAPO-34)

(a) BAPO-34 is prepared from a reaction mixture having a composition, expressed in terms of the molar oxide ratios of the components of the reaction mixture, of:

1.0–2.0 TEAOH:0.05–0.2 $B_2O_3$:0.5–1.0 $Al_2O_3$: 0.5–1.0 $P_2O_5$:40–100 $H_2O$ where "TEAOH" denotes tetraethylammonium hydroxide.

The reaction mixture is digested by placing the reaction mixture in a sealed stainless steel pressure vessel and heating it at an effective temperature and for an effective time to produce the BAPO-34 product. Solids are then recovered by filtration, washed with water and dried in air at room temperature.

The BAPO-34 product's chemical analysis shows the BAPO-34 product contains boron, aluminum and phosphorus in amounts within the hexagonal compositional area defined by points A, B, C, D, E and F of FIG. 1.

The X-ray powder diffraction pattern of a BAPO-34 product is characterized by the following data:

| 2θ | d(Å) | Relative Intensity |
|---|---|---|
| 9.4–9.65 | 9.41–9.17 | s–vs |
| 15.90–16.2 | 5.57–5.47 | vw–m |
| 17.85–18.4 | 4.97–4.82 | w–s |
| 20.30–20.9 | 4.37–4.25 | m–vs |
| 24.95–25.4 | 3.57–3.51 | vw–s |
| 30.30–30.8 | 2.95–2.90 | w–s |

(b) The X-ray powder diffraction pattern for a calcined BAPO-34 is also characterized by the X-ray pattern of part (a).

(c) When the calcined BAPO-34 of part (b) is utilized in adsorption capacity studies using a standard McBain- Bakr gravimetric adsorption apparatus the measurements are made on a sample after activation at 350° C. in vacuum. The following data are used in the adsorption studies:

| Adsorbate | Kinetic Diameter(Å) | Pressure (Torr) | Temp, °C. | Wt. % Adsorbed* |
|---|---|---|---|---|
| $O_2$ | 3.46 | 100 | −183 | 13 |
| $O_2$ | 3.46 | 750 | −183 | 18 |
| n-Hexane | 4.3 | 100 | 24 | 6 |
| $H_2O$ | 2.65 | 4.3 | 24 | 15 |
| $H_2O$ | 2.65 | 20 | 24 | 21 |

*typical amount adsorbed

The pore diameter of BAPO-34 is about 4.3 Å.

EXAMPLE 10

(Preparation of BAPO-44)

(a) BAPO-44 is prepared from a reaction mixture having a composition, expressed in terms of the molar oxide ratios of the components of the reaction mixture, of:

1.0–2.0 CHA:0.05–0.2 $B_2O_3$:0.5–1.0 $Al_2O_3$: 0.5–1.0 $P_2O_5$:40–100 $H_2O$ where "CHA" denotes cyclohexylamine.

The reaction mixture is digested by placing the reaction mixture in a sealed stainless steel pressure vessel and heating it at an effective temperature and for an effective time to produce the BAPO-44 product. Solids are then recovered by filtration, washed with water and dried in air at room temperature.

The BAPO-44 product's chemical analysis shows the BAPO-44 product contains boron, aluminum and phosphorus in amounts within the hexagonal compositional area defined by points A, B, C, D, E and F of FIG. 1.

The X-ray powder diffraction pattern of a BAPO-44 product is characterized by the following data:

| 2Θ | d(Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

(b) The X-ray powder diffraction pattern for a calcined BAPO-44 is also characterized by the X-ray pattern of part (a).

(c) When the calcined BAPO-44 of part (b) is utilized in adsorption capacity studies using a standard McBain-Bakr gravimetric adsorption apparatus the measurements are made on a sample after activation at 350° C. in vacuum The following data are used in the adsorption studies:

| Adsorbate | Kinetic Diameter(Å) | Pressure (Torr) | Temp, °C. | Wt. % Adsorbed* |
|---|---|---|---|---|
| $O_2$ | 3.46 | 100 | −183 | 13 |
| $O_2$ | 3.46 | 750 | −183 | 16 |
| n-Hexane | 4.3 | 100 | 24 | 2 |
| $H_2O$ | 2.65 | 4.3 | 24 | 15 |
| $H_2O$ | 2.65 | 20 | 24 | 17 |

*typical amount adsorbed

The pore diameter of BAPO-44 is about 4.3 Å.

PROCESS APPLICATIONS

The BAPO compositions of the present invention are, in general, hydrophilic and adsorb water preferentially over common hydrocarbon molecules such as paraffins, olefins and aromatic species, e.g., benzene, xylenes and cumene. Thus the present molecular sieve compositions as a class are useful as desiccants in such adsorption separation/purification processes as natural gas drying and cracked gas drying. Water is also preferentially adsorbed over the so-called permanent gases such as carbon dioxide, nitrogen, oxygen and hydrogen. These BAPOs are therefore suitably employed in the drying of reformer hydrogen streams and in the drying of oxygen, nitrogen or air prior to liquefaction.

The present BAPO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art (e.g. ion exchange or impregnation) and used, for example, in fabricating catalyst compositions having silica or alumina bases. Of the general class, those species having pores larger than about 4 Å are preferred for catalytic applications.

Among the hydrocarbon conversion reactions catalyzed by BAPO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using BAPO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. (204° C. to 441° C.) using molar ratios of hydrogen to hydrocarbon in the range of between 2 and 80, pressures between 10 and 3500 p.s.i.g. (0.171 to 24.23 MPa.), and a liquid hourly space velocity (LHSV) of from 0.1 to 20, preferably 1.0 to 10.

The BAPO catalyst compositions employed in hydrocracking are also suitable for use in reforming processes in which the hydrocarbon feedstocks contact the catalyst at temperatures of from about 700° F. to 1000° F. (371° C. to 538° C.), hydrogen pressures of from 100 to 500 p.s.i.g. (0.791 to 3.448 MPa.), LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 200° F. to 600° F. (93° C. to 316° C.), preferably 300° F. to 550° F. (149° C. to 288° C.) with an LHSV value of from about 0.2 to 1.0. Hydrogen (H) is supplied to the reactor in admixture with the hydrocarbon ($H_c$) feedstock in molar proportions (H/$H_c$) of between 1 and 5.

At somewhat higher temperatures, i.e. from about 650° F. to 1000° F. (343° C. to 538° C.), preferably 850° F. to 950° F. (454° C. to 510° C.) and usually at somewhat lower pressures within the range of about 15 to 50 p.s.i.g. (205 to 446 KPa.), the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present BAPO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400 to 750° F. (204 to 399° C.), pressures in the range of 100 to 2000 p.s.i.g. (0.791 to 13.89 MPa.) and LHSV values in the range of 0.1 to 15.

Catalytic cracking processes are preferably carried out with BAPO compositions using feedstocks such as gas oils, heavy naphthas, deasphalted crude oil residua, etc., with gasoline being the principal desired product. Temperature conditions of 850 to 1100° F. (454 to 593° C.), LHSV values of 0.5 to 10 and pressure conditions of from about 0 to 50 p.s.i.g. (101 to 446 KPa.) are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the BAPO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. (427°–538° C.) are employed at moderate hydrogen pressures of about 300–1000 p.s.i.g. (2.176.895 MPa.), other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like. Any of these may contain up to about 5 wt. percent of sulfur and up to about 3 wt. percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than with a feed containing less organonitrogen compounds. Consequently, the conditions under which denitrogenation, desulfurization and/or hydrocracking can be most expeditiously accomplished in any given situation are necessarily determined in view of the characteristics of the feedstocks, in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F. (260°–482° C.), while paraffins, napthenes and alkyl aromatics are isomerized at temperatures of 700°–1000° F. (371°–538° C.). Particularly desirable isomerization reactions contemplated herein include the conversion of n-heptene and/or n-octane to iso-heptanes and/or iso-octanes, butane to iso-butane, methylcyclopentane to cyclohexane, meta-xylene and/or ortho-xylene to para-xylene, 1-butene to 2-butene and/or iso-butene, n-hexene to iso-hexene, cyclohexene to methylcyclopentene etc. The preferred form of the catalyst is a combination of the BAPO with polyvalent metal compounds (such as sulfides) of metals of Group II-A, Group II-B and rare earth metals. For alkylation and dealkylation processes, the BAPO compositions having pores of at least 5Å are preferred. When employed for dealkylation of alkyl aromatics, the temperature is usually at least 350° F. (177° C.) and ranges up to a temperature at which substantial cracking of the feedstock or conversion products occurs, generally up to about 700° F. (371° C.). The temperature is preferably at least 450° F. (232° C.) and not greater than the critical temperature of the compound undergoing dealkylation. Pressure conditions are applied to retain at least the aromatic feed in the liquid state. For alkylation, the temperature can be as low as 250° F. (121° C.) but is preferably at least 350° F. (177° C.). In the alkylation of benzene, toluene and xylene, the preferred alkylating agents are olefins such as ethylene and propylene.

We claim:

1. Crystalline molecular sieves having three-dimensional microporous framework structures of $BO_2$, $AlO_2$ and $PO_2$ tetrahedral units having an empirical chemical composition on an anhydrous basis expressed by the formula:

mR: $(B_xAl_yP_z)O_2$ wherein "R" represents at least one organic templating agent present in the intracrystalline pore system; "m" represents the molar amount of "R" present per mole of $(B_xAl_yP_z)O_2$ and has a value of zero to about 0.3; "x", "y" and "z" represent the mole fractions of boron, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables A, B1, B2, C to H and J to V:

TABLE A (BAPO-5)

| 2θ | d (Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B1*

(BAPO-11)

| 2θ | d (Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

*as-synthesized form

TABLE B2*

(BAPO-11)

| 2θ | d (Å) | Relative Intensity |
|---|---|---|
| 8.0–8.2 | 11.05–10.78 | w–s |
| 9.5–9.9 | 9.31–8.93 | m–s |
| 16.0–16.2 | 5.54–5.47 | s–vs |
| 21.6–21.9 | 4.12–4.06 | vs |
| 22.1–22.6 | 4.02–3.93 | m–s (doublet) |
| 23.4–23.7 | 3.80–3.75 | m–s |

*calcined form

TABLE C (BAPO-14)

| 2θ | d (Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D (BAPO-16)

| 2θ | d (Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |

TABLE D-continued (BAPO-16)

| 2θ | d (Å) | Relative Intensity |
|---|---|---|
| 29.7–30.05 | 3.008–2.974 | w–m |

TABLE E (BAPO-17)

| 2θ | d (Å) | Relative Intensity |
|---|---|---|
| 7.7–7.8 | 11.5–11.3 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F (BAPO-18)

| 2θ | d (Å) | Relative Intensity |
|---|---|---|
| 9.6–9.65 | 9.21–9.16 | vs |
| 15.5–15.6 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G (BAPO-20)

| 2θ | d (Å) | Relative Intensity |
|---|---|---|
| 13.7–14.25 | 6.46–6.22 | m–vs |
| 19.55–20.0 | 4.54–4.44 | w–s |
| 24.05–24.5 | 3.70–3.63 | m–vs |
| 34.3–35.0 | 2.614–2.564 | vw–w |
| 42.5–43.0 | 2.127–2.103 | vw–w |

TABLE H (BAPO-31)

| 2θ | d (Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

(BAPO-33)

| 2θ | d (Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

(BAPO-33)

| 2θ | d (Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| | (BAPO-34) | |
|---|---|---|
| 2θ | d (Å) | Relative Intensity |
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

TABLE M

| | (BAPO-35) | |
|---|---|---|
| 2θ | d (Å) | Relative Intensity |
| 10.8–11.1 | 8.19–7.97 | m |
| 17.2–17.4 | 5.16–5.10 | s–vs |
| 21.0–21.25 | 4.23–4.18 | m–s |
| 21.8–22.0 | 4.08–4.04 | vs |
| 31.8–32.2 | 2.814–2.788 | m |

TABLE N

| | (BAPO-36) | |
|---|---|---|
| 2θ | d (Å) | Relative Intensity |
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE O

| | (BAPO-37) | |
|---|---|---|
| 2θ | d (Å) | Relative Intensity |
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| | (BAPO-39) | |
|---|---|---|
| 2θ | d (Å) | Relative Intensity |
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| | (BAPO-40) | |
|---|---|---|
| 2θ | d (Å) | Relative Intensity |
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| | (BAPO-41) | |
|---|---|---|
| 2θ | d (Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |

TABLE R-continued

| | (BAPO-41) | |
|---|---|---|
| 2θ | d (Å) | Relative Intensity |
| 23.1–23.4 | 3.82–3.80 | w–m |
| 25.5–25.9 | 3.493–3.440 | w–m |

TABLE S

| | (BAPO-42) | |
|---|---|---|
| 2θ | d (Å) | Relative Intensity |
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |
| 30.05–30.25 | 2.974–2.955 | m–s |

TABLE T

| | (BAPO-44) | |
|---|---|---|
| 2θ | d (Å) | Relative Intensity |
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

| | (BAPO-46) | |
|---|---|---|
| 2θ | d (Å) | Relative Intensity |
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| | (BAPO-47) | |
|---|---|---|
| 2θ | d (Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w |

2. Crystalline molecular sieves according to claim 1 wherein the mole fractions of boron, aluminum and phosphorus present as tetrahedral oxides are within the tetragonal compositional area defined by points a, b, c and d of FIG. 2.

3. Crystalline molecular sieves according to claim 2 wherein the mole fraction of boron is not greater than about 0.3.

4. The crystalline molecular sieves of claim 1 or 2 having a characteristic X-ray powder diffraction pattern which contains at least the d-spacings set forth in Table A given in claim 1.

5. The crystalline molecular sieves of claim 1 or 2 having a characteristic X-ray powder diffraction pattern which contains at least the d-spacings set forth in Table B1 or B2 given in claim 1.

6. The crystalline molecular sieves of claim 5 wherein the X-ray powder diffraction pattern set forth in Table B1 or B2 contains at least the d-spacings set forth in one of the following Tables B1A, B2B and B2C:

TABLE B1A

(BAPO-11)

| 2θ | d (Å) | Relative Intensity 100 × I/I$_o$ |
|---|---|---|
| 8.1 | 10.877 | 47 |
| 9.5 | 9.33 | 78 |
| 13.3 | 6.67 | 22 |
| 15.7 | 5.63 | 47 |
| 16.3 | 5.42 | 7 |
| 19.1 | 4.66 | 8 |
| 20.5 | 4.33 | 60 |
| 21.1 | 4.21 | 100 |
| 21.9 | 4.07 | 7 |
| 22.2 | 4.00 | 63 |
| 22.6 | 3.93 | 59 |
| 22.8 | 3.90 | 62 |
| 23.3 | 3.82 | 90 |
| 24.6 | 3.62 | 7 |
| 24.8 | 3.59 | 10 |
| 26.4 | 3.37 | 13 |
| 26.7 | 3.34 | 21 |
| 28.4 | 3.14 | 6 |
| 28.7 | 3.11 | 17 |
| 29.2 | 3.06 | 5 |
| 29.6 | 3.02 | 8 |
| 31.6 | 2.83 | 10 |
| 33.0 | 2.71 | 18 |
| 34.3 | 2.61 | 12 |
| 35.9 | 2.50 | 3 |
| 36.6 | 2.45 | 7 |
| 37.7 | 2.39 | 9 |
| 37.9 | 2.37 | 12 |
| 39.5 | 2.28 | 4 |

TABLE B2B

(BAPO-11)

| 2θ | d (Å) | Relative Intensity 100 × I/I$_o$ |
|---|---|---|
| 8.1 | 10.92 | 73 |
| 9.6 | 9.22 | 60 |
| 9.8 | 9.02 | 66 |
| 12.8 | 6.90 | 33 |
| 13.1 | 6.76 | 16 |
| 16.1 | 5.51 | 73 |
| 19.5 | 4.55 | 12 |
| 19.9 | 4.46 | 30 |
| 20.3 | 4.38 | 14 |
| 21.3 | 4.17 | 32 |
| 21.8 | 4.07 | 100 |
| 22.2 | 4.00 | 63 |
| 22.4 | 3.96 | 72 |
| 23.0 | 3.86 | 23 |
| 23.5 | 3.79 | 65 |
| 24.0 | 3.71 | 14 |
| 25.8 | 3.45 | 21 |
| 27.7 | 3.22 | 15 |
| 27.9 | 3.20 | 12 |
| 29.6 | 3.01 | 22 |
| 29.8 | 3.00 | 26 |
| 30.4 | 2.94 | 14 |
| 31.8 | 2.81 | 10 |
| 32.7 | 2.74 | 29 |

TABLE B2C

(BAPO-11)

| 2θ | d (Å) | Relative Intensity 100 × I/I$_o$ |
|---|---|---|
| 8.1 | 10.94 | 21 |
| 9.9 | 8.98 | 51 |
| 12.8 | 6.89 | 27 |
| 14.7 | 6.03 | 19 |
| 16.1 | 5.49 | 77 |
| 19.5 | 4.54 | 12 |
| 19.9 | 4.46 | 32 |
| 21.9 | 4.06 | 100 |
| 22.2 | 4.00 | 48 |
| 22.5 | 3.95 | 57 |

TABLE B2C-continued

(BAPO-11)

| 2θ | d (Å) | Relative Intensity 100 × I/I$_o$ |
|---|---|---|
| 23.6 | 3.77 | 61 |
| 24.0 | 3.70 | 13 |
| 24.3 | 3.66 | 13 |
| 25.8 | 3.45 | 24 |
| 26.8 | 3.33 | 11 |
| 27.3 | 3.27 | 13 |
| 28.1 | 3.18 | 50 |
| 29.8 | 3.00 | 27 |
| 30.4 | 2.94 | 16 |
| 32.7 | 2.74 | 27. |

7. The crystalline molecular sieves of claim 1 or 2 having a characteristic X-ray powder diffraction pattern which contains at least the d-spacings set forth in Table C given in claim 1.

8. The crystalline molecular sieves of claim 1 or 2 having a characteristic X-ray powder diffraction pattern which contains at least the d-spacings set forth in Table D given in claim 1.

9. The crystalline molecular sieves of claim 1 or 2 having a characteristic X-ray powder diffraction pattern which contains at least the d-spacings set forth in Table E given in claim 1.

10. The crystalline molecular sieves of claim 1 or 2 having a characteristic X-ray powder diffraction pattern which contains at least the d-spacings set forth in Table F given in claim 1.

11. The crystalline molecular sieves of claim 10 wherein the X-ray powder diffraction pattern set forth in Table F contains at least the d-spacings set forth in the following Table FA:

TABLE FA

(BAPO-18)

| 2θ | d (Å) | Relative Intensity 100 × I/I$_o$ |
|---|---|---|
| 9.6 | 9.20 | 100 |
| 10.5 | 8.41 | 4 |
| 11.0 | 8.02 | 4 |
| 13.2 | 6.71 | 6 |
| 14.0 | 6.31 | 5 |
| 14.9 | 5.96 | 4 |
| 15.6 | 5.69 | 24 |
| 17.1 | 5.20 | 44 |
| 17.5 | 5.07 | 6 |
| 17.9 | 4.95 | 7 |
| 19.7 | 4.51 | 4 |
| 20.2 | 4.39 | 18 |
| 21.0 | 4.22 | 38 |
| 22.2 | 4.01 | 10 |
| 24.5 | 3.64 | 8 |
| 24.9 | 3.57 | 5 |
| 26.2 | 3.40 | 8 |
| 26.5 | 3.36 | 8 |
| 27.0 | 3.31 | 7 |
| 28.2 | 3.17 | 4 |
| 30.1 | 2.97 | 10 |
| 30.8 | 2.90 | 9 |
| 31.4 | 2.85 | 9 |
| 31.8 | 2.81 | 5 |
| 32.5 | 2.76 | 13. |

12. The crystalline molecular sieves of claim 1 or 2 having a characteristic X-ray powder diffraction pattern which contains at least the d-spacings set forth in Table G given in claim 1.

13. The crystalline molecular sieves of claim 1 or 2 having a characteristic X-ray powder diffraction pattern which contains at least the d-spacings set forth in Table H given in claim 1.

14. The crystalline molecular sieves of claim 1 or 2 having a characteristic X-ray powder diffraction pattern which contains at least the d-spacings set forth in Table J given in claim 1.

15. The crystalline molecular sieves of claim 1 or 2 having a characteristic X-ray powder diffraction pattern which contains at least the d-spacings set forth in Table K given in claim 1.

16. The crystalline molecular sieves of claim 1 or 2 having a characteristic X-ray powder diffraction pattern which contains at least the d-spacings set forth in Table L given in claim 1.

17. The crystalline molecular sieves of claim 1 or 2 having a characteristic X-ray powder diffraction pattern which contains at least the d-spacings set forth in Table M given in claim 1.

18. The crystalline molecular sieves of claim 1 or 2 having a characteristic X-ray powder diffraction pattern which contains at least the d-spacings set forth in Table N given in claim 1.

19. The crystalline molecular sieves of claim 1 or 2 having a characteristic X-ray powder diffraction pattern which contains at least the d-spacings set forth in Table O given in claim 1.

20. The crystalline molecular sieves of claim 1 or 2 having a characteristic X-ray powder diffraction pattern which contains at least the d-spacings set forth in Table P given in claim 1.

21. The crystalline molecular sieves of claim 1 or 2 having a characteristic X-ray powder diffraction pattern which contains at least the d-spacings set forth in Table Q given in claim 1.

22. The crystalline molecular sieves of claim 1 or 2 having a characteristic X-ray powder diffraction pattern which contains at least the d-spacings set forth in Table R given in claim 1.

23. The crystalline molecular sieves of claim 1 or 2 having a characteristic X-ray powder diffraction pattern which contains at least the d-spacings set forth in Table S given in claim 1.

24. The crystalline molecular sieves of claim 1 or 2 having a characteristic X-ray powder diffraction pattern which contains at least the d-spacings set forth in Table T given in claim 1.

25. The crystalline molecular sieves of claim 1 or 2 having a characteristic X-ray powder diffraction pattern which contains at least the d-spacings set forth in Table U given in claim 1.

26. The crystalline molecular sieves of claim 1 or 2 having a characteristic X-ray powder diffraction pattern which contains at least the d-spacings set forth in Table V given in claim 1.

27. Process for preparing crystalline molecular sieves having three-dimensional microporous framework structures of $BO_2$, $AlO_2$ and $PO_2$ tetrahedral units having an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; "x", "y" and "z" represent the mole fractions of boron, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables A, B1, B2, C to H and J to V:

TABLE A

| 2θ | (BAPO-5) d (Å) | Relative Intensity |
|---|---|---|
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B1*

| 2θ | (BAPO-11) d (Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | m–s |
| 22.5–22.9 | 3.95–3.92 | m–s |
| 23.0–23.4 | 3.87–3.80 | m–vs |

*as-synthesized form

TABLE B2*

| 2θ | (BAPO-11) d (Å) | Relative Intensity |
|---|---|---|
| 8.0–8.2 | 11.05–10.78 | w–s |
| 9.5–9.9 | 9.31–8.93 | m–s |
| 16.0–16.2 | 5.54–5.47 | s–vs |
| 21.6–21.9 | 4.12–4.06 | vs |
| 22.1–22.6 | 4.02–3.93 | m–s (doublet) |
| 23.4–23.7 | 3.80–3.75 | m–s |

*calcined form

TABLE C

| 2θ | (BAPO-14) d (Å) | Relative Intensity |
|---|---|---|
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| 2θ | (BAPO-16) d (Å) | Relative Intensity |
|---|---|---|
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E

| 2θ | (BAPO-17) d (Å) | Relative Intensity |
|---|---|---|
| 7.7–7.8 | 11.5–11.3 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| 2θ | (BAPO-18) d (Å) | Relative Intensity |
|---|---|---|
| 9.6–9.65 | 9.21–9.16 | vs |
| 15.5–15.6 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| 2θ | (BAPO-20) d (Å) | Relative Intensity |
|---|---|---|
| 13.7–14.25 | 6.46–6.22 | m–vs |
| 19.55–20.0 | 4.54–4.44 | w–s |
| 24.05–24.5 | 3.70–3.63 | m–vs |
| 34.3–35.0 | 2.614–2.564 | vw–w |
| 42.5–43.0 | 2.127–2.103 | vw–w |

TABLE H

| 2θ | (BAPO-31) d (Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

| 2θ | (BAPO-33) d (Å) | Relative Intensity |
|---|---|---|
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| 2θ | (BAPO-33) d (Å) | Relative Intensity |
|---|---|---|
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| 2θ | (BAPO-34) d (Å) | Relative Intensity |
|---|---|---|
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

TABLE M

| 2θ | (BAPO-35) d(Å) | Relative Intensity |
|---|---|---|
| 10.8–11.1 | 8.19–7.97 | m |
| 17.2–17.4 | 5.16–5.10 | s–vs |
| 21.0–21.25 | 4.23–4.18 | m–s |

TABLE M-continued

| 2θ | (BAPO-35) d(Å) | Relative Intensity |
|---|---|---|
| 21.8–22.0 | 4.08–4.04 | vs |
| 31.8–32.2 | 2.814–2.788 | m |

TABLE N

| 2θ | (BAPO-36) d(Å) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE O

| 2θ | (BAPO-37) d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

| 2θ | (BAPO-391) d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

| 2θ | (BAPO-40) d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

| 2θ | (BAPO-41) d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

| 2θ | (BAPO-42) d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |

TABLE S-continued

| | (BAPO-42) | |
|---|---|---|
| 2Θ | d(Å) | Relative Intensity |
| 30.05–30.25 | 2.974–2.955 | m–s |

TABLE T

| | (BAPO-44) | |
|---|---|---|
| 2Θ | d(Å) | Relative Intensity |
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

| | (BAPO-46) | |
|---|---|---|
| 2Θ | d(Å) | Relative Intensity |
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

| | (BAPO-47) | |
|---|---|---|
| 2Θ | d(Å) | Relative Intensity |
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w | which process comprises providing a reaction mixture composition at an effective temperature and for an effective time sufficient to produce said molecular sieves, said reaction mixture composition comprising sources of boron, aluminum and phosphorus, and being expressed in terms of molar oxide ratios as follows:

$$aR: (B_xAl_yP_z)O_2: bH_2O$$

wherein "R" is an organic templating agent; "a" is an effective amount of "R" greater than zero; "b" has a value of from zero to about 500; and "u", "v" and "w" represent the mole fractions, respectively, of boron, aluminum and phosphorus in the $(B_xAl_yP_z)O_2$ constituent, and each has a value of at least 0.01.

28. The process of claim 27 wherein "u", "v" and "w" are within the pentagonal compositional area defined by points F, G, H, I and J of FIG. 3.

29. The process of claim 27 wherein said reaction mixture composition comprises from about 0.5 to about 2.0 moles of $B_2O_3$ per mole of $P_2O_5$.

30. The process of claim 27 wherein said reaction mixture composition comprises from about 0.75 to about 1.25 moles of $Al_2O_3$ per mole of $P_2O_5$.

31. The process of claim 27 wherein "a" has a value of greater than zero to about 6.

32. The process of claim 31 wherein "a" has a value not greater than about 1.0.

33. The process of claim 27 wherein "b" has a value of not greater than about 20.

34. The process of claim 33 wherein "b" has a value of not greater than about 10.

35. Process according to claim 27 wherein the source of phosphorus in the reaction mixture is orthophosphoric acid.

36. Process according to claim 27 wherein the source of phosphorus in the reaction mixture is orthophosphoric acid and the source of aluminum is at least one compound selected from the group consisting of pseudo-boehmite and aluminum alkoxides.

37. Process according to claim 36 wherein the aluminum alkoxide is aluminum isopropoxide.

38. Process according to claim 27 wherein the source of boron is selected from the group consisting of acids or boron, alkoxides, hydroxides, oxides, chlorides, bromides, iodides, nitrates, sulfates, acetates, formates, organo-boron compounds and mixtures thereof.

39. Process according to claim 38 wherein the source of boron is boric acid or trimethylborate.

40. Process according to claim 27 wherein the sources of boron, aluminum and phosphorus are combined to form an amorphous material containing all three of these elements, and thereafter the amorphous material is heated to produce a crystalline molecular sieve according to claim 1.

41. Process according to claim 27 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

42. Process according to claim 27 wherein the organic templating agent is an amine.

43. Process according to claim 27 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N,-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric $[(C_{14}H_{32}N_2)(OH)_2]_x$ quaternary ammonium salt wherein x has a value of at least 2.

44. Molecular sieves prepared by calcining crystalline molecular sieves having three-dimensional microporous framework structures of $BO_2$, $AlO_2$ and $PO_2$ tetrahedral units having an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; "x", "y" and "z" represent the mole fractions of boron, aluminum and phosphorus, respectively, present as tetrahedral oxides, said mole fractions being such that they are within the hexagonal compositional area defined by points A, B, C, D, E and F of FIG. 1, said crystalline molecular sieves having a characteristic X-ray powder diffraction pattern which contains at least the d-spacings set forth in one of the following Tables A, B1, B2, C to H and J to V:

TABLE A

| 2θ | d(Å) | Relative Intensity |
|---|---|---|
| (BAPO-5) | | |
| 7.3–7.65 | 12.1–11.56 | m–vs |
| 19.5–19.95 | 4.55–4.46 | m–s |
| 20.9–21.3 | 4.25–4.17 | m–vs |
| 22.2–22.6 | 4.00–3.93 | w–vs |
| 25.7–26.15 | 3.47–3.40 | w–m |

TABLE B1*

| 2θ | d(Å) | Relative Intensity |
|---|---|---|
| (BAPO-11) | | |
| 9.3–9.65 | 9.51–9.17 | m–s |
| 20.2–20.6 | 4.40–4.31 | m–s |
| 20.9–21.3 | 4.25–4.17 | s–Vs |
| 22.0–22.5 | 4.04–3.95 | m–s |
| 22.5–22.9 | 3.95–3.92 | m–s |
| 23.0–23.4 | 3.87–3.80 | m–vs |

*as-synthesized form

TABLE B2*

| 2θ | d(Å) | Relative Intensity |
|---|---|---|
| (BAPO-11) | | |
| 8.0–8.2 | 11.05–10.78 | w–s |
| 9.5–9.9 | 9.31–8.93 | m–s |
| 16.0–16.2 | 5.54–5.47 | s–vs |
| 21.6–21.9 | 4.12–4.06 | vs |
| 22.1–22.6 | 4.02–3.93 | m–s(doublet) |
| 23.4–23.7 | 3.80–3.75 | m–s |

*calcined form

TABLE C

| 2θ | d(Å) | Relative Intensity |
|---|---|---|
| (BAPO-14) | | |
| 8.6–8.9 | 10.3–9.93 | vs |
| 13.0 | 6.81 | w |
| 21.9–22.2 | 4.06–4.00 | w |
| 25.4 | 3.51 | w |
| 27.5 | 3.24 | w |
| 29.7 | 3.01 | w |

TABLE D

| 2θ | D(Å) | Relative Intensity |
|---|---|---|
| (BAPO-16) | | |
| 11.3–11.6 | 7.83–7.63 | m–vs |
| 18.7–18.9 | 4.75–4.70 | w–s |
| 21.9–22.3 | 4.06–3.99 | m–vs |
| 26.5–27.0 | 3.363–3.302 | w–m |
| 29.7–30.05 | 3.008–2.974 | w–m |

TABLE E

| 2θ | D(Å) | Relative Intensity |
|---|---|---|
| (BAPO-17) | | |
| 7.7–7.8 | 11.5–11.3 | vs |
| 13.4 | 6.61 | s–vs |
| 15.5–15.55 | 5.72–5.70 | s |
| 19.65–19.7 | 4.52–4.51 | w–s |
| 20.5–20.6 | 4.33–4.31 | vs |
| 31.8–32.00 | 2.812–2.797 | w–s |

TABLE F

| 2θ | d(Å) | Relative Intensity |
|---|---|---|
| (BAPO-18) | | |
| 9.6–9.65 | 9.21–9.16 | vs |
| 15.5–15.6 | 5.72–5.70 | m |
| 16.9–17.1 | 5.25–5.19 | m |
| 20.15–20.25 | 4.41–4.39 | m |
| 20.95–21.05 | 4.24–4.22 | m |
| 31.8–32.5 | 2.814–2.755 | m |

TABLE G

| 2θ | d(Å) | Relative Intensity |
|---|---|---|
| (BAPO-20) | | |
| 13.7–14.25 | 6.46–6.22 | m–vs |
| 19.55–20.0 | 4.54–4.44 | w–s |
| 24.05–24.5 | 3.70–3.63 | m–vs |
| 34.3–35.0 | 2.614–2.564 | vw–w |
| 42.5–43.0 | 2.127–2.103 | vw–w |

TABLE H

| 2θ | d(Å) | Relative Intensity |
|---|---|---|
| (BAPO-31) | | |
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE J*

| 2θ | d(Å) | Relative Intensity |
|---|---|---|
| (BAPO-33) | | |
| 9.25–9.55 | 9.56–9.26 | w–m |
| 12.5–12.9 | 7.08–6.86 | vs |
| 16.9–17.3 | 5.25–5.13 | w–m |
| 20.45–20.9 | 4.34–4.25 | w–m |
| 23.85–24.25 | 3.73–3.67 | w–m |
| 26.05–26.35 | 3.42–3.38 | w–m |
| 27.3–27.6 | 3.27–3.23 | vs |

*as-synthesized form

TABLE K*

| 2θ | d(Å) | Relative Intensity |
|---|---|---|
| (BAPO-33) | | |
| 13.15–13.4 | 6.73–6.61 | vs |
| 18.05–18.35 | 4.91–4.83 | m |
| 18.4–18.6 | 4.82–4.77 | m |
| 26.55–26.7 | 3.36–3.34 | m |
| 32.0–32.1 | 2.80–2.79 | m |

*calcined form

TABLE L

| 2θ | d(Å) | Relative Intensity |
|---|---|---|
| (BAPO-34) | | |
| 9.4–9.65 | 9.41–9.17 | s–vs |
| 15.9–16.2 | 5.57–5.47 | vw–m |
| 17.85–18.4 | 4.97–4.82 | w–s |
| 20.3–20.9 | 4.37–4.25 | m–vs |
| 24.95–25.4 | 3.57–3.51 | vw–s |
| 30.3–30.8 | 2.95–2.90 | w–s |

TABLE M

| 2θ | d(Å) | Relative Intensity |
|---|---|---|
| (BAPO-35) | | |
| 10.8–11.1 | 8.19–7.97 | m |
| 17.2–17.4 | 5.16–5.10 | s–vs |
| 21.0–21.25 | 4.23–4.18 | m–s |

TABLE M-continued

(BAPO-35)

| 2θ | d(Å) | Relative Intensity |
|---|---|---|
| 21.8–22.0 | 4.08–4.04 | vs |
| 31.8–32.2 | 2.814–2.788 | m |

TABLE N

(BAPO-36)

| 2θ | d(Å) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

TABLE O

(BAPO-37)

| 2θ | d(Å) | Relative Intensity |
|---|---|---|
| 6.1–6.3 | 14.49–14.03 | vs |
| 15.5–15.7 | 5.72–5.64 | w–m |
| 18.5–18.8 | 4.80–4.72 | w–m |
| 23.5–23.7 | 3.79–3.75 | w–m |
| 26.9–27.1 | 3.31–3.29 | w–m |

TABLE P

(BAPO-39)

| 2θ | d(Å) | Relative Intensity |
|---|---|---|
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

TABLE Q

(BAPO-40)

| 2θ | d(Å) | Relative Intensity |
|---|---|---|
| 7.5–7.7 | 11.79–11.48 | vw–m |
| 8.0–8.1 | 11.05–10.94 | s–vs |
| 12.4–12.5 | 7.14–7.08 | w–vs |
| 13.6–13.8 | 6.51–6.42 | m–s |
| 14.0–14.1 | 6.33–6.28 | w–m |
| 27.8–28.0 | 3.209–3.187 | w–m |

TABLE R

(BAPO-41)

| 2θ | d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.440 | w–m |

TABLE S

(BAPO-42)

| 2θ | d(Å) | Relative Intensity |
|---|---|---|
| 7.15–7.4 | 12.36–11.95 | m–vs |
| 12.5–12.7 | 7.08–6.97 | m–s |
| 21.75–21.9 | 4.09–4.06 | m–s |
| 24.1–24.25 | 3.69–3.67 | vs |
| 27.25–27.4 | 3.273–3.255 | s |

TABLE S-continued

(BAPO-42)

| 2θ | d(Å) | Relative Intensity |
|---|---|---|
| 30.05–30.25 | 2.974–2.955 | m–s |

TABLE T

(BAPO-44)

| 2θ | d(Å) | Relative Intensity |
|---|---|---|
| 9.4–9.55 | 9.41–9.26 | vs |
| 13.0–13.1 | 6.81–6.76 | w–m |
| 16.0–16.2 | 5.54–5.47 | w–m |
| 20.6–20.85 | 4.31–4.26 | s–vs |
| 24.3–24.4 | 3.66–3.65 | w–vs |
| 30.7–30.95 | 2.912–2.889 | w–s |

TABLE U

(BAPO-46)

| 2θ | d(Å) | Relative Intensity |
|---|---|---|
| 7.2–8.1 | 12.3–10.9 | vs |
| 21.2–21.8 | 4.19–4.08 | w–m |
| 22.5–23.0 | 3.95–3.87 | vw–m |
| 26.6–27.2 | 3.351–3.278 | vw–w |
| 28.5–29.0 | 3.132–3.079 | vw–w |

TABLE V

(BAPO-47)

| 2θ | d(Å) | Relative Intensity |
|---|---|---|
| 9.4 | 9.41 | vs |
| 15.9–16.0 | 5.57–5.54 | w–m |
| 20.5–20.6 | 4.33–4.31 | s |
| 24.5–24.7 | 3.63–3.60 | w |
| 25.8–25.9 | 3.45–3.44 | w |
| 30.4–30.5 | 2.940–2.931 | w, | said molecular sieves having an intracrystalline pore system, said calcination being effected at a temperature sufficiently high to remove at least some of any organic templating agent present in the intracrystalline pore system.

45. Crystalline molecular sieves having three-dimensional microporous framework structures of $BO_2$, $AlO_2$ and $PO_2$ tetrahedral units having an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; and "x", "y" and "z" represent the mole fractions of boron, aluminum and phosphorus, respectively, present as tetrahedral oxides, said mole fractions being such that they are within the hexagonal compositional area defined by points A, B, C, D, E and F of FIG. 1.

46. Crystalline molecular sieves according to claim 45 wherein the mole fractions of boron, aluminum and phosphorus present as tetrahedral oxides are within the tetragonal compositional area defined by points a, b, c and d of FIG. 2.

47. Crystalline molecular sieves according to claim 46 wherein the mole fraction of boron is not greater than about 0.3.

48. Process for preparing crystalline molecular sieves having three-dimensional microporous framework structures of $BO_2$, $AlO_2$ and $PO_2$ tetrahedral units having an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; "x", "y" and "z" represent the mole fractions of boron, aluminum and phosphorus, respectively, present as tetrahedral oxides, said mole fractions being such that they are within the hexagonal compositional area defined by points A, B, C, D, E and F of FIG. 1, which process comprises providing a reaction mixture composition at an effective temperature and for an effective time sufficient to produce said molecular sieves, said reaction mixture composition comprising sources of boron, aluminum and phosphorus, and being expressed in terms of molar oxide ratios as follows:

$$aR: (B_uAl_vP_w)O_2:bH_2O$$

wherein "R" is an organic templating agent; "a" is an effective amount of "R" greater than zero; "b" has a value of from zero to about 500; and "u", "v" and "w" represent the mole fractions, respectively, of boron, aluminum and phosphorus in the $(B_uAl_vP_w)O_2$ constituent, and each has a value of at least 0.01.

49. The process of claim 48 wherein "u", "v" and "w" are within the pentagonal compositional area defined by points F, G, H, I and J of FIG. 3.

50. The process of claim 48 wherein said reaction mixture composition comprises from about 0.5 to about 2.0 moles of $B_2O_3$ per mole of $P_2O_5$.

51. The process of claim 48 wherein said reaction mixture composition comprises from about 0.75 to about 1.25 moles of $Al_2O_3$ per mole of $P_2O_5$.

52. The process of claim 48 wherein "a" has a value of greater than zero to about 6.

53. The process of claim 52 wherein "a" has a value not greater than about 1.0.

54. The process of claim 48 wherein "b" has a value of not greater than about 20.

55. The process of claim 54 wherein "b" has a value of not greater than about 10.

56. Process according to claim 48 wherein the source of phosphorus in the reaction mixture is orthophosphoric acid.

57. Process according to claim 48 wherein the source of phosphorus in the reaction mixture is orthophosphoric acid and the source of aluminum is at least one compound selected from the group consisting of pseudo-boehmite and aluminum alkoxides.

58. Process according to claim 57 wherein the aluminum alkoxide is aluminum isopropoxide.

59. Process according to claim 48 wherein the source of boron is selected from the group consisting of acids or boron, alkoxides, hydroxides, oxides, chlorides, bromides, iodides, nitrates, sulfates, acetates, formates, organo-boron compounds and mixtures thereof.

60. Process according to claim 59 wherein the source of boron is boric acid or trimethylborate.

61. Process according to claim 48 wherein the sources of boron, aluminum and phosphorus are combined to form an amorphous material containing all three of these elements, and thereafter the amorphous material is heated to produce a crystalline molecular sieve according to claim 45.

62. Process according to claim 48 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

63. Process according to claim 48 wherein the organic templating agent is an amine.

64. Process according to claim 48 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diaziabicyclo-(2,2,2) octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric quaternary ammonium salt $[(C_{14}H_{32}N_2)(OH)_2]_x$ wherein x has a value of at least 2.

65. Molecular sieves prepared by calcining crystalline molecular sieves having three-dimensional microporous framework structures of $BO_2$, $AlO_2$ and $PO_2$ tetrahedral units having an empirical chemical composition on an anhydrous basis expressed by the formula:

$$mR: (B_xAl_yP_z)O_2$$

wherein "R" represents at least one organic templating agent present in the intracrystalline pore system; "m" represents the molar amount of "R" present per mole of $(B_xAl_yP_z)O_2$ and has a value of zero to about 0.3; "x", "y" and "z" represent the mole fractions of boron, aluminum and phosphorous, respectively, present as tetrahedral oxides, said mole fractions being such that they are within the hexagonal compositional area defined by points A, B, C, D, E and F of FIG. 1, said molecular sieves having an intracrystalline pore system, said calcination being effected at a temperature sufficiently high to remove at least some of any organic templating agent present in the intracrystalline pore system.

* * * * *